United States Patent [19]

Sperber et al.

[11] Patent Number: 5,665,312
[45] Date of Patent: Sep. 9, 1997

[54] BLOOD ANALYSIS SYSTEM HAVING BLOOD STORAGE, TRANSPORT AND AUTOMATIC SLIDE-MAKING CAPABILITIES

[75] Inventors: Cynthia J. Sperber, Fort Lauderdale; Daniel Dashui Gao, Miami, both of Fla.; Marshall D. Graham, Nicholasville, Ky.

[73] Assignee: Coulter International Corp., Miami, Fla.

[21] Appl. No.: 557,229

[22] Filed: Nov. 14, 1995

[51] Int. Cl.⁶ .......................... G01N 35/10; B05C 11/08
[52] U.S. Cl. ............................ 422/81; 422/63; 422/65; 422/66; 422/67; 422/68.1; 422/103; 436/43; 436/46; 436/49; 436/52; 436/174; 436/180; 118/100; 118/236; 427/2.11
[58] Field of Search .................... 422/63, 65, 66, 422/67, 73, 81, 100, 68.1, 103; 436/43, 44, 46, 49, 50, 54, 55, 52, 174, 180; 427/2.1, 2.11; 118/100, 236, 238

[56] References Cited

U.S. PATENT DOCUMENTS

| | | |
|---|---|---|
| 3,995,022 | 11/1976 | Heanley et al. ............. 424/3 |
| 4,016,828 | 4/1977 | Maher, Jr. et al. ............ 118/6 |
| 4,096,824 | 6/1978 | Levine et al. ............. 118/100 |
| 4,120,262 | 10/1978 | Adler et al. ............. 118/642 |
| 4,303,611 | 12/1981 | Jessop ............. 422/65 |
| 4,378,333 | 3/1983 | Laipply ............. 422/100 |
| 4,494,479 | 1/1985 | Drury et al. ............. 118/120 |
| 4,902,476 | 2/1990 | Gordon et al. ............. 422/46 |
| 5,209,903 | 5/1993 | Kanamori et al. . |
| 5,415,840 | 5/1995 | Sano et al. ............. 422/67 |
| 5,470,534 | 11/1995 | Imai et al. ............. 422/67 |
| 5,494,828 | 2/1996 | Leopando ............. 436/180 |
| 5,519,635 | 5/1996 | Miyake et al. ............. 364/497 |

*Primary Examiner*—Long V. Le
*Attorney, Agent, or Firm*—Warren W. Kurz

[57] ABSTRACT

A blood analyzer system is provided with improved slide making capability by coupling a blood analyzer apparatus to an automatic slidemaking apparatus by means of a clinically effective blood specimen transport assembly, which includes a blood conduit forming a curvilinear flow path that imparts a substantial angular velocity component to blood moving therein. The system enables a blood analyzer portion and a smear slide portion of a given sample to be aspirated with physical and temporal proximity.

17 Claims, 6 Drawing Sheets

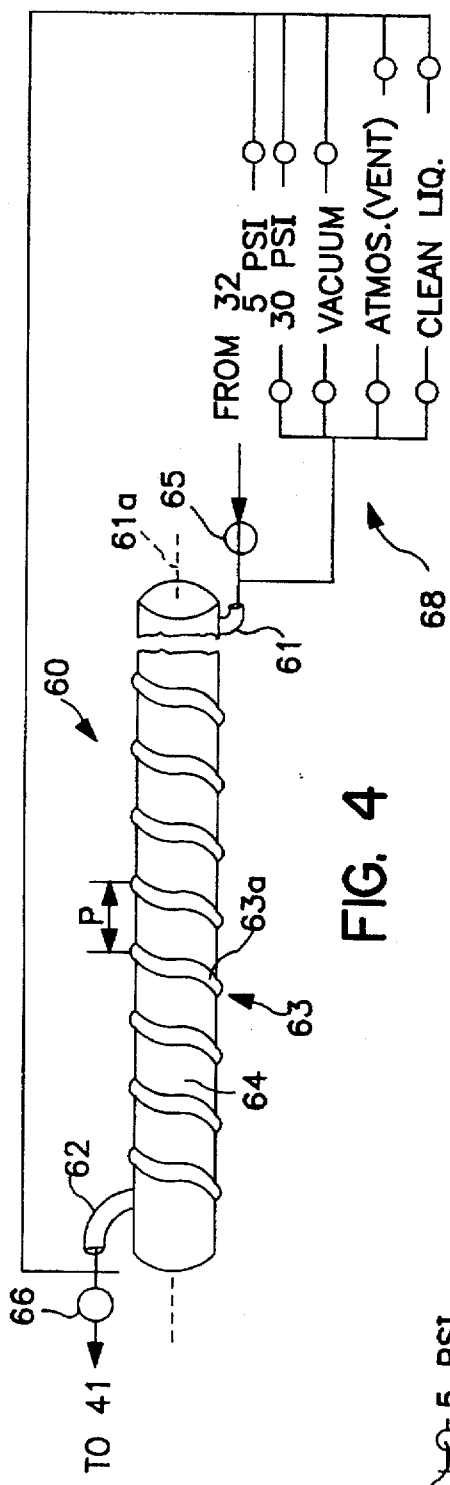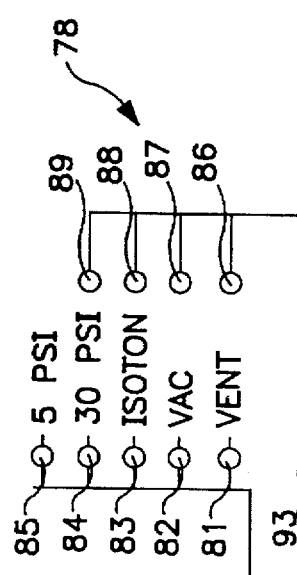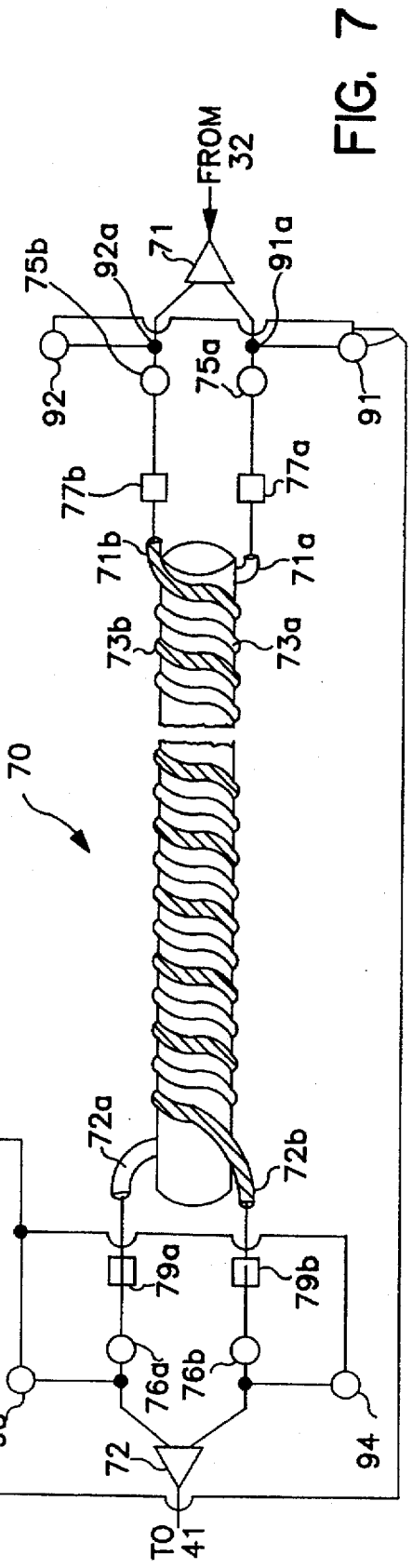
FIG. 4
FIG. 7

BLOOD ANALYSIS SYSTEM HAVING BLOOD STORAGE, TRANSPORT AND AUTOMATIC SLIDE-MAKING CAPABILITIES

CROSS-REFERENCE TO RELATED APPLICATIONS

Reference is made to the commonly assigned U.S. Patent Applications filed concurrently herewith, and presently pending the respective disclosures of which being incorporated herein by reference: (1) U.S. Ser. No. 08/557,226, entitled "Improved Apparatus and Method for Automated Production of Blood Smear Slides"; (2) U.S. Ser. No. 08/555,688, entitled "Improved Method and Apparatus for the Preparation of Microscope Slides"; (3) U.S. Ser. No. 08/55,687, entitled "Pinch Pump for Dispensing Fluid from a Flexible Fluid Conduit"; (4) U.S. Ser. No. 08/557,228, entitled "Improved Method and Apparatus for Drying Blood Smear Slides"; and (5) U.S. Ser. No. 08/557,230, entitled "Cassette for Blood Smear Slides and Cooperative Slide Ejection Assembly".

BACKGROUND OF THE INVENTION

1. Field of Invention

The present invention relates to blood analyzing systems of the kind that detect and analyze the composition of whole blood samples. More particularly, it relates to an improved blood analyzing system that is capable of automatically storing and transporting blood specimens and, upon preprogrammed and/or operator-determined command, of providing a blood smear on a microscope slide, e.g. for further study, verification and/or analysis.

2. Discussion of Prior Art

Currently, medical diagnosis is assisted greatly by systems which analyze whole blood samples to determine their detail compositional make-up. For example, the COULTER® STKS Blood Analyzer utilizes a unique hematology system in which three independent energy probes (viz. direct current, radio frequency and a stable helium-neon laser) cooperate to measure a blood cell's volume, conductivity and light scatter. Memory and control systems of the analyzer store and process detected cell information to provide the user with data (e.g, screen displays or print-outs) indicating the relative proportions of different cell types/ populations constituting respective blood samples. Thus, in its various modes the analyzer can provide a wide variety of blood information, including hemograms, five part differential white blood cell counts and reticulocyte enumeration and analysis. While such information is useful in itself to diagnosticians, it sometimes occurs that a blood smear slide would be useful for further microscopically analyzing the sample and/or verifying the results of the analyzer system.

To produce a blood smear slide, it is necessary to withdraw an additional portion of blood from the sample container (e.g., a specimen vial), dispense a drop from that portion on a microscope slide and spread the drop on the slide to form a blood smear. U.S. Pat. No. 5,209,903, describes a system for automating these steps. It includes a conveyor assembly for moving racks of blood vials, first past one or more separate blood analyzers, and then past an automated slide-making apparatus. Each of these separate apparatus includes its own blood aspiration assembly, as well as the necessary supply, disposal and cleaning devices and fluids that are required to handle successive blood specimens in a clinical manner. In addition, each separate apparatus comprises its own bar code reading system to identify the individual vials, and its own vial handling mechanisms to present vials from the conveyor to its bar code reader and aspirator. In different site installations, the analyzer and slidemaker apparatus will often be arranged in different configurations, so the conveyor system for transporting vial racks are frequently custom designed or individually modified for each installation, which can present significant costs.

In addition to the structural and operational complexities presented by the '903 patent system, problems can be presented because the blood aspirations for the slidemaker and the different analyzer apparatus occur at different sample regions and at different times. Thus, because the vials containing the samples are moved to the different apparatus and repeatedly pierced with different probes of different aspirator devices, the blood specimen portions may be withdrawn from the different regions of the vials and the blood specimens from those different regions may have different characteristics. Similarly, because of the required vial transport periods between the analyzers and slidemakers, the specimens withdrawn can have temporal distinctions. Moreover, in the '903 system it is necessary for the blood smear testing of each vial in a given rack to await the completion of analyzer work on all other vials in the rack, which reduces significantly the system's flexibility regarding individual samples.

To obviate the many disadvantages of the approach that conveys sample containers between analyzers and the slidemaker, we have discovered a new approach for providing automated slide-making capabilities for blood analyzers, an approach that employs the clinically effective transport of blood specimens, via tubing, from a single aspiration site to both the analyzer apparatus and the slide-maker apparatus. Moreover, we have found that while blood is transported safely by plastic tubing for short distances, problems of sample integrity (such as cell morphology distortion, sample dilution and platelet losses) can occur when whole blood samples are transported over extended paths, e.g. between an analyzer apparatus and automatic slide-making apparatus. Also, we have found when blood samples are retained in a relatively immobile status for any substantial time, the cells begin to settle in a manner that can affect the homogeneity of the sample. If such changes occur to significant extents, a blood smear slide that is formed from such transported blood is not properly representative of the blood analyzed by the automated analyzer system, and no useful results will be achieved by microscope examination.

SUMMARY OF THE INVENTION

One significant purpose of the present invention is to provide for automated blood analysis systems such as described above, new capability for automatically producing blood smear slides of their tested samples, in a manner providing sample integrity, homogeneity and identification. In a related aspect, the present invention provides a unique system for transporting blood samples over extended distances in a manner that minimizes changes of the samples. This transport system provides further advantage by maintaining sample homogeneity over the extended storage periods, thereby enabling data analysis and communication between subsystems, e.g., between an automatic blood analyzer and an automated slide maker.

Thus, in one important aspect, the present invention constitutes an improved construction for an automated blood analysis system of the kind having: (i) means for receiving a blood sample containers, (ii) processing means for automatically aspirating a first blood specimen portion from the received sample container, to produce data characteristic of such specimen portion, and (iii) control means for analyzing said data. Such improved construction includes an apparatus for automatically producing a blood smear slide from blood in the sample container and comprises: (a) means for automatically producing a blood smear slide from a smear specimen portion of sample blood and (b) means for automatically transmitting a smear specimen portion of sample blood from the sample containers in said receiving means to said slide producing means.

In another aspect the present invention constitutes a system for transporting specimen portions of whole blood for extended distances and comprises: (a) means defining a specimen portion inlet, (b) means defining a specimen portion outlet and (c) blood conduit means extending between said inlet and outlet and including means forming a curvilinear flow path that imparts a substantial angular velocity component to blood moving therein.

BRIEF DESCRIPTION OF THE DRAWINGS

The subsequent detailed description of the invention refers to the accompanying drawings wherein like reference characters denote like parts:

FIG. 4 is a schematic elevation view of a portion of one specimen transmission system for practice of the present invention;

FIG. 7 is a schematic elevation view of another preferred specimen transmission system in accord with the present invention.

DETAILED DESCRIPTION OF PREFERRED EMBODIMENTS

Figure 1:
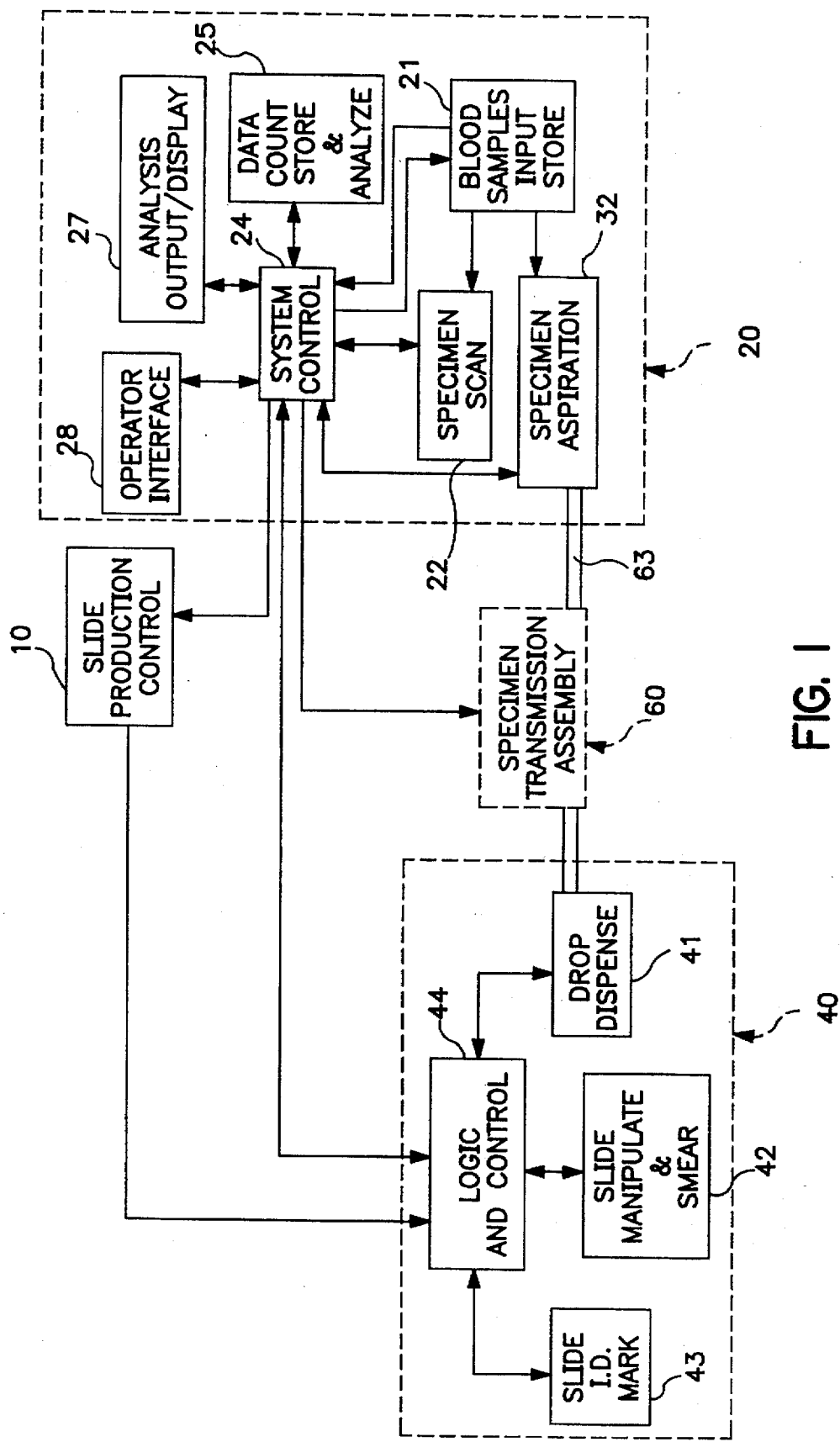
FIG. 1 is a block diagram indicating the overall relation of the different apparatus components which comprise the improved blood analysis system of the present invention.
Figure 2:
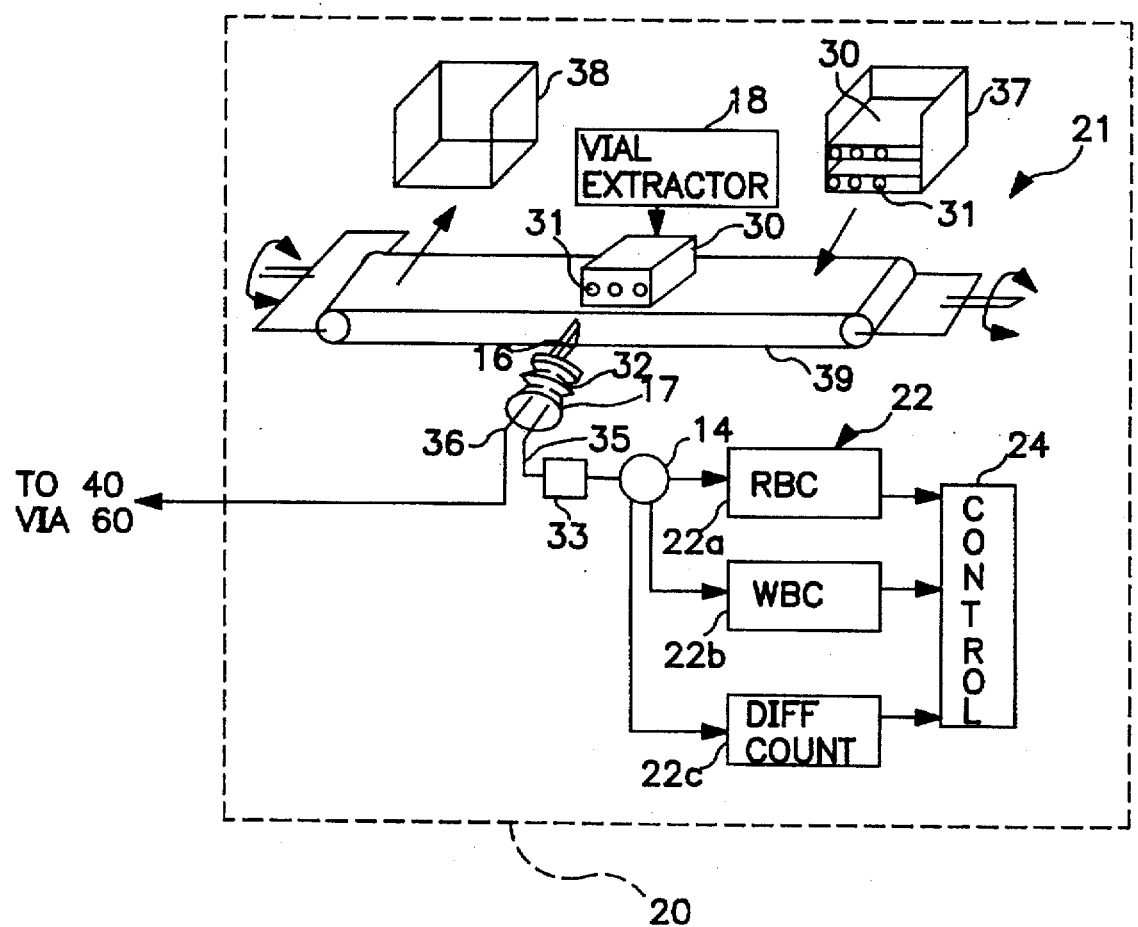
FIG. 2 is a schematic perspective view illustrating portions of one preferred blood analysis apparatus for practice of the present invention.

Referring to FIG. 1, there is illustrated by diagram, a blood analysis system incorporating improved constructions according to the present invention. In this embodiment, the systems includes two mainframe device, viz., an automated blood analyzer 20 and an automated slidemaker 40. Devices 20 and 40 are physically coupled together by a specimen transmission assembly 60; they are electronically coupled to a slide production control module 10. The blood analyzer 20 preferably comprises the COULTER® STKS Blood Analyzer available from Coulter Corporation of Miami, Fla. Such an analyzer includes means for receiving a plurality of blood sample containers, indicated by blood sample input-store 21 in FIG. 1, and shown schematically in FIG. 2 to include input and output bins 37, 38 and a conveyor system 39. Each of the bins is adapted to receive a plurality of racks 30 of blood sample vials 31. As illustrated schematically, the vial racks are fed onto the conveyor system 39 which moves the racks 30 to an aspiration station, aligned with the aspirator needle 16 contained within a bellows assembly 17 adapted to facilitate needle cleansing. A vial extraction assembly 18 moves the rack vials sequentially into punctured, aspirating relation with aspirator needle. As schematically illustrated in FIG. 2, the conveyor assembly 39 is periodically tilted about its longitudinal axis to provide mixing of the blood in vials conveyed thereby. After each vial of a rack has been aspirated in sequence, the rack is moved to the output bin 38, and a new rack is moved onto the conveyor from the input bin. The analyzer 20 further includes blood specimen processor subsystem which includes the specimen aspiration means 32 for withdrawing blood specimens to be analyzed from the respective sample container 31 (see FIG. 2), and scan means 22 for scanning such specimens to detect specimen characteristic data, e.g. red blood cell, white blood cell and differential count, as provided by subsystems 22a, 22b, 22c, respectively. The data from the subsystems of processor 22 is stored and analyzed, e.g. by microprocessor subsystem 25, as operated with inputs and controls from system control 24. After analytical computations are completed, results of the data can be printed out or displayed by subsystem 27, e.g. CRT display screen, and are forwarded to slide production control 10. Control 10 can embody an algorithm(s) that will decide if non-normal data conditions exist such as to initiate a slide production operation. The operator interface 28 also can provide access for the user to input instructions, e.g. the desire for a slide to be made from the specimen.

Figure 3:
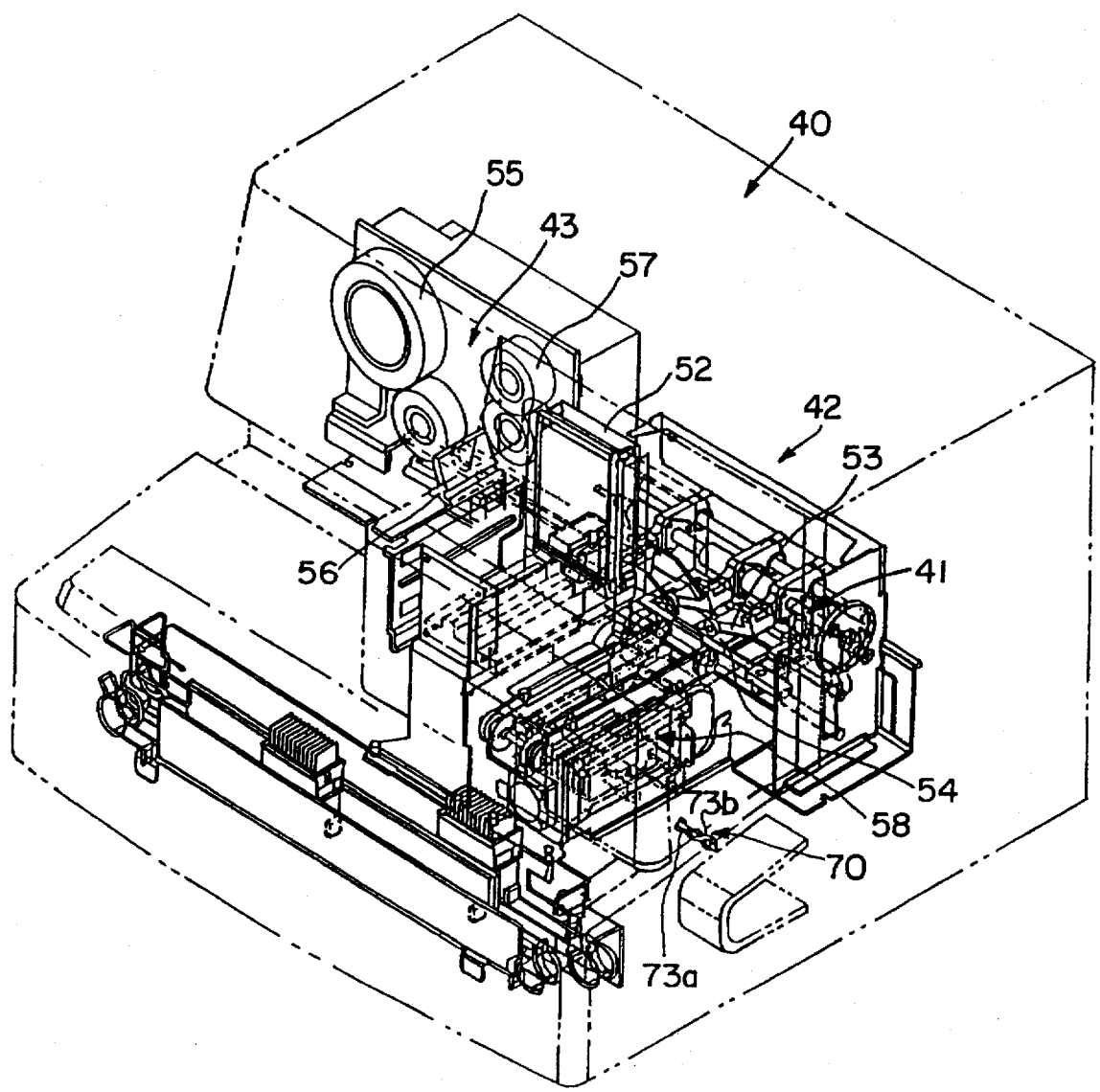
FIG. 3 is a schematic perspective view illustrating portions of one preferred automatic slide-making apparatus for practice of the present invention.

The automated slidemaker 40 is shown in more detail in FIG. 3 and in general comprises a drop dispensing subsystem 41, a slide manipulation and smear subsystem 42, and a slide ID mark subsystem 43. As illustrated in FIG. 1, logic and control 44 is coupled to operate these subsystems. FIG. 3 also shows a slide cassette 52 from which slides are extracted and presented to a manipulation assembly 53 (sometimes referred to as a "slide truck"), which in turn grasps and transports the slides to a movable transport platform 54 (sometimes referred to as a "slide shuttle"). The transport platform moves slides first to a marking station 43 comprising a label supply 55, a print media supply 57 and printer 56. The platform then moves a labeled slide to the drop dispense station 41 where a smear specimen drop is dispensed. Thereafter, the transport platform moves to a smear station where the slide manipulation assembly moves between the two positions illustrated. In moving between these two positions, a blood drop is smeared with the edge of an angularly oriented, next successive slide from the cassette. After the smear step, the slide is moved onto the belt of a dryer station 58 and then to an outloader system (not shown). The details of the slidemaker apparatus construction and function are described in concurrently filed, U.S. Ser. No. 08/57,226, entitled "Improved Apparatus and Method for Automated Production of Blood Smear Slides", which is incorporated herein by reference.

FIG. 4 shows a preferred assembly 60 for automatically transmitting specimen blood between separate mainframe apparatus, such as 20 and 40, with minimized sample degradation and improved homogeneity. Assembly 60 comprises a blood conduit 63 having an inlet 61 for successively receiving smear specimen portions respectively from different blood sample containers in the analyzer apparatus 20, and an outlet 62 for delivering such smear specimen portions to the dispensing station 41 of apparatus 40. In accord with the present invention, conduit 63 winds around a central longitudinal axis 61a to provide a curvilinear flow path that imparts substantial angular velocity components to blood moving therein. Such configuration is referred to herein as "generally helical".

In one preferred embodiment of such assembly, conduit means 63 comprises a plastic tube which is wound, generally in the form of a helix, around a support cylinder 64 extending between the mainframe apparatus. One preferred tubing comprises a laboratory silicone type commercially sold by Dow Corning Corporation under the trademark SILASTIC. We have found that providing tubing with inner diameter on the order of 0.020 to about 0.040 inches minimizes the loss of platelets due to attachment to tube walls. In one embodiment a tube of 18 inches linear length and inner diameter of 0.04 inches is helically wound around a cylinder with length of 10 inches having a 0.25 inch diameter. The resulting helix has about 10 turns and a pitch of about 2 inches. However, those skilled in the art will appreciate that other generally helical configurations will function to provide a curvilinear flow path that imparts substantial angular velocity components to blood transported thereby.

Figure 6:
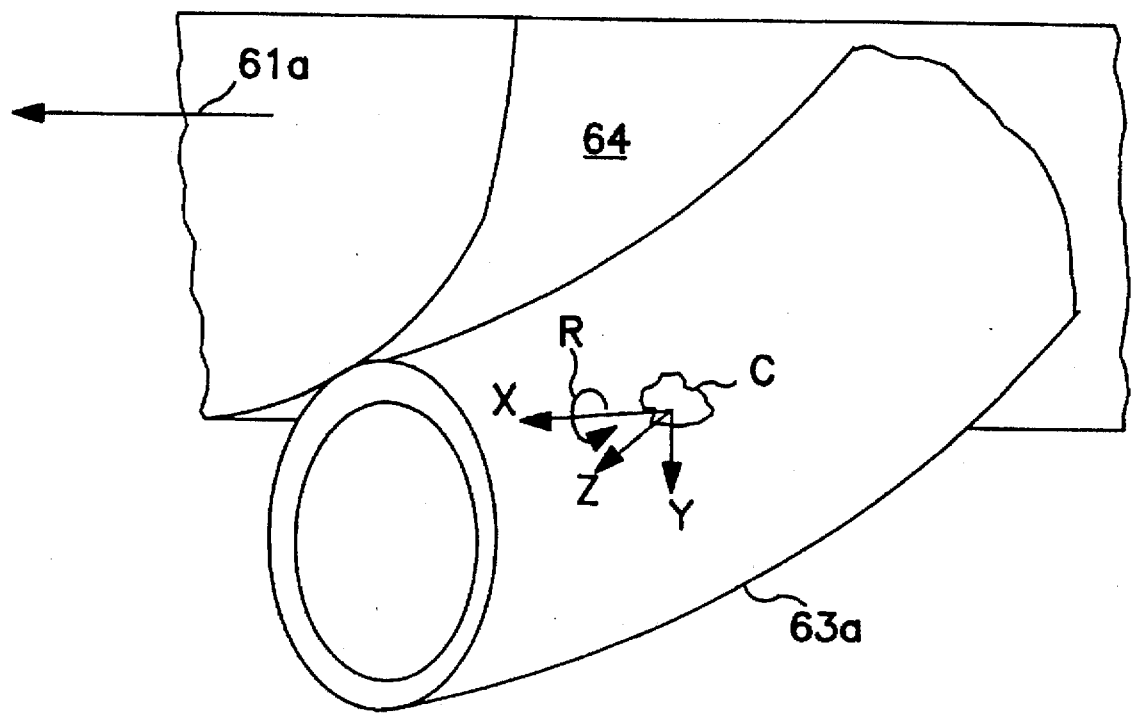
FIGS. 5 and 6 are diagrams useful for explaining certain aspects of the present invention.
Figure 5:
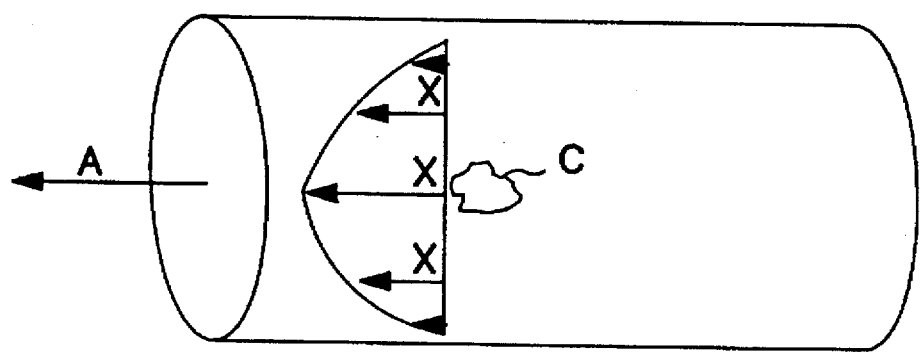

FIG. 5 illustrates prior art systems wherein blood is transported with a primarily linear velocity in the direction of a transport conduits longitudinal axis. We have observed that this linear velocity profile allows cells to settle. The linear or rectilinear velocity gives rise to cells settling quickly because of gravitational forces. Such settling has the effect of altering the homogeneity of the blood as it moves between the blood analyzer 20 and slide maker 40. Moreover, settling can alter the cell morphology due to the relatively lengthy contact time between the cells and internal wall of the conduit as the cells are moved through the conduit. Referring to FIG. 6, it can be seen that the helical path provided by the assembly of the present invention provides, as well as "x", "y" and "z" linear velocity components, continuous radial accelerations to blood transported from inlet to outlet. Thus, the blood has a continuous angular velocity R and rectilinear velocities which vary in magnitude and direction along the path shown schematically in FIG. 6. This angular velocity R and changing rectilinear velocities are believed to cause a tumbling movement of blood cells C during transport, which minimizes specimen degradation in comparison to the specimen quality provided by the differential "x" velocity profile incident to straight tubing transport, as illustrated in FIG. 5. In addition, "y" and "z" components provided during the movement of blood around a curvilinear winding such as helix, provides more effective stirring of the blood than is provided by a straight line path, whereby the homogeneity of the blood is better preserved between the time it was aspirated and the time it is used to produce a blood smear.

Figure 8:
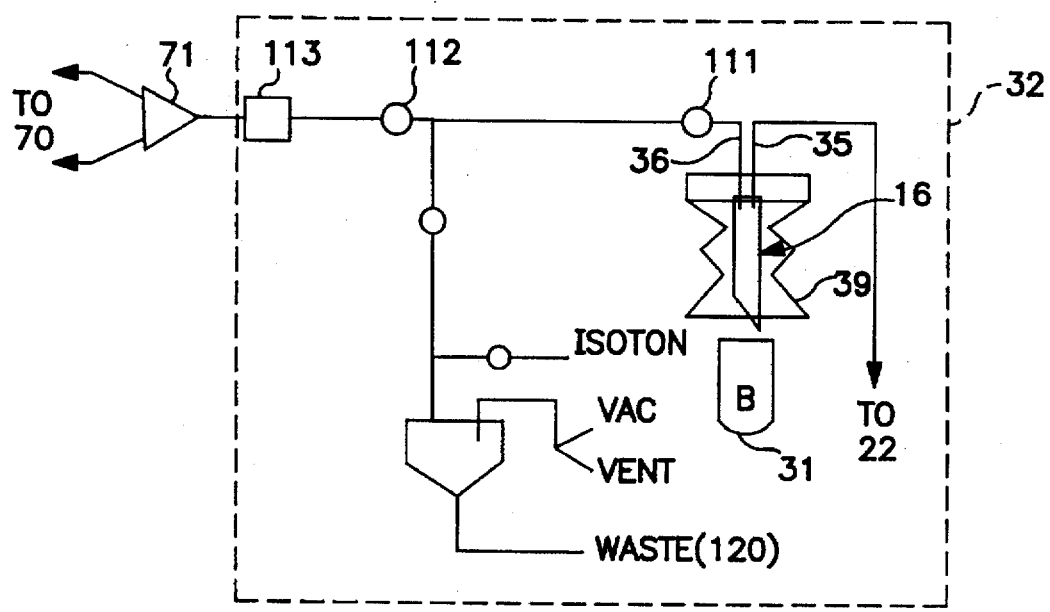
FIGS. 8 and 9 are schematic fluid flow diagrams illustrating preferred constructions for cooperating with the FIG. 7 embodiment in practice of the present invention.

In general operation of the overall system, a plurality of blood sample containers, e.g. sealed glass vials 31, are inserted into the specimen container receiving system (shown in FIG. 2) of analyzer apparatus 20. The analyzer's aspirator system 32, 35, 33 is actuated to withdraw a sample of blood through one channel 35 (see FIG. 8) of needle 16, to divider valve 14 for processing and analysis by subsystem 22. A blood smear specimen is next aspirated through a second channel 36 (see FIG. 8) of needle 16 and introduced into blood storage and transmission system 60 (see FIG. 4). For example, inlet valve 65 is opened and negative pressure from one of a bank of sources 68 is coupled to outlet end 62 to move the smear specimen portion into the helical path provided by the windings of tube 63. Because the first blood specimen for analyzer 20 and the second blood specimen, for transport by system 60, are both aspirated by needle 16, the specimens are from substantially the same location within a given vial 31. Also, because those specimens are taken sequentially from a given vial 31 (before any other vials are sampled), the specimens for analysis by apparatus 20 and for slide smear preparation by apparatus 40 are temporally proximate.

The apparatus 20 proceeds to complete analyzation of the first blood specimen for which a corresponding blood smear specimen portion now resides in the transmission assembly. To prevent settling during the period pending a decision to make a slide, the fluid pressure source of assembly 60 is cycled to produce forward and reverse movement of the blood along the helical conduit 63. This can be accomplished by alternately coupling inlet and outlet regions to negative pressure and vent ports of fluid sources 68. When a decision is made by the operator (e.g. based on study of the analyzer data) or automatically (e.g. based on flag output parameters), to make a blood smear on a slide, a smear cycle initiation signal is relayed to control 44 of apparatus 40 and to the system control 24 of apparatus 20. Recycling of the blood sample continues, forward and rearward, along the helical path, while specific smear data is forwarded to and implemented by apparatus 40. For example, specimen identification data is forwarded to logic and control 44 to assure that a properly identified slide is presented to dispense station 41, and other data (e.g. smear speed information) is forwarded to assure that a blood smear is made according to an algorithm which takes into account various blood parameters (e.g. hematocrit).

When these procedures have been completed, the specimen recycling ends and the smear specimen is forwarded to dispensing station 41, e.g. by opening outlet valve 66 and coupling inlet region 61 to the 5 psi pressure of fluid source bank 68. After discarding a leading portion of blood specimen, a metered blood drop is dispensed on the marked slide. Thereafter, a cleaning solution from source bank 68 is washed through the transport tubing to prepare it for receiving its next smear sample portion from the analyzer 20. Finally, a drying is effected by injection of 30 psi air from source bank 68 through the conduit. In the event that analyzation determines a blood smear is not required the transmission system 60 forwards the smear specimen to a waste sump in apparatus 40, instead of to the dispensing station 41.

Figure 9:
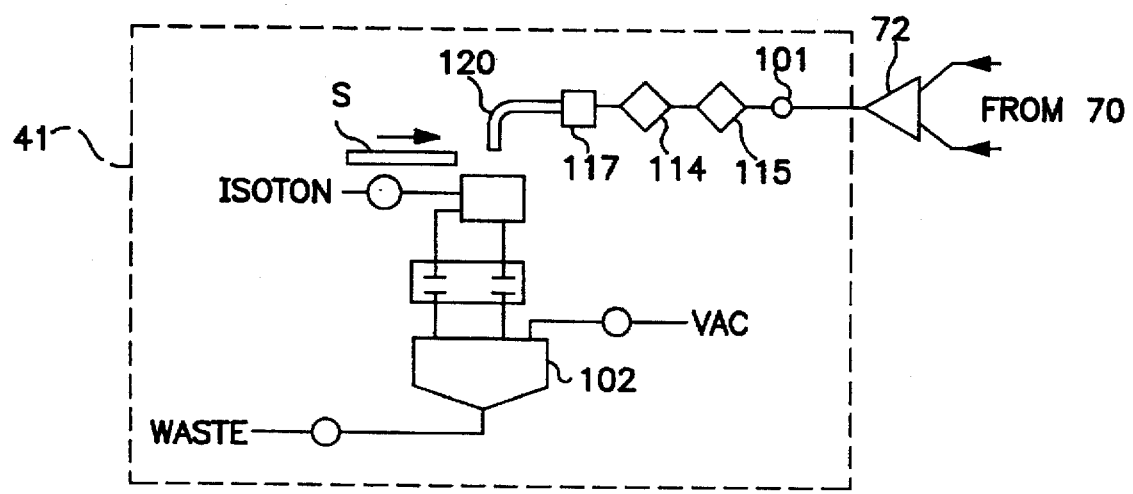

In order to maintain commensurate speed with the operational speeds of apparatus 20 and 40, an alternative embodiment of the transmission system 70 (see FIGS. 7–9) incorporates a plurality (here two) helical tubes 73a, 73b, which are coupled in parallel between three way inlet valve 71 and three way outlet valve 72 so that one path can be receiving, recycling and outputting a blood sample, while another path is being cleaned. For this purpose, each of helical tubes 73a, 73b has an inlet end 71a, 71b and outlet end 72a, 72b couplable to the bank of fluid sources 78 as shown in FIG. 7, by solenoid valves 91, 92, 93 and 94, respectively. Specific sources within fluid source bank 78 are selectable for the inlet ends 71a, 71b by solenoid valves 81, 82, 83, 84 and 85 and for the outlet ends 72a, 72b by solenoid valves 86, 87, 88 and 89. Branch inlet solenoid valves 75a, 75b are located respectively just upstream of upstream blood detector devices (e.g. photodetectors) 77a, 77b and branch outlet solenoid valves 76a, 76b are located respectively just downstream of downstream blood detectors 79a, 79b.

In accord with a highly preferred feature of the present invention, both the FIGS. 4 and 7 fluid systems have controls that operate the valves thereof to provide means for introducing an intervening gas sector at a position after a lead sector of a blood smear specimen portion in the helical tubing. In n one preferred mode, the gas sector is introduced behind about 50 μl of forward specimen blood. This feature of the present invention allows the forward specimen sector to pick up residual cleaning solution from the tube and to isolate this residue from the trailing specimen sector. The forward or lead specimen sector is directed to the sump 102 of apparatus 40 and the trailing sector is metered by valves 114, 115 for dispensing by station 41. The mode of creating such intermediate gas sector will be clear from the following description of a cycle of operation of the FIGS. 7–9 system.

A sequence of operation commences after analyzer 20 has withdrawn its specimen, as described above. Thus, first a negative pressure is coupled to the aspirator passage side 35 of needle 16 (with needle passage 36 coupled to vent) to withdraw an analyzer blood portion for the analyzer to perform its functions. Immediately after aspiration through passage 35 is finished, a smear-specimen portion is withdrawn from the vial 31 by coupling the passage 36 in needle 16 to vacuum, e.g. via solenoid valves 87, 93, 76a, 75a, 71, 112 and 111. Blood is withdrawn from the vial and flows along the vacuum passage until the lead end of the smear-specimen portion reaches blood detector 113, at which time aspiration vacuum is signaled to stop and the needle 16 is withdrawn from vial 31. The withdrawn smear-specimen sample portion continues to be advanced until its lead end is detected by detector 77a, whereupon valve 87 terminates the vacuum. At this stage about 50 microliters of blood resides between detector 77a and branch inlet "T" fitting 91a. The line to valve 91 is next coupled to atmospheric pressure via vent valve 86, and air is injected into a region behind the leading 50 microliter segment, which is now drawn forward by vacuum via 87. With the protective gas region separating the trail end of the lead segment from the remainder of the smear-specimen, the valve 75a is opened, valve 91 is closed, and vacuum 87 draws the remainder of the sample forward until detector 79a detects the lead segment, at which point valves 75a and 76a are both closed. At this stage, cleaning liquid is introduced to clean upstream of valve 71, and a second specimen can be introduced into reservoir 73b in a similar manner to that just described. The specimen in the reservoir 73a now comprises a 50 microliter lead segment and a 200 microliter trailing segment, separated by a gas sector that positively maintains separation between those blood specimen segments. The segments are then recycled forward and rearward between closed valves 75a, 76a by alternately coupling valves 91 and 93 to vacuum and vent (91 to 81, 82 and 93 to 87,86). The magnitudes of the vacuum are selected to cause a blood speed along the helical tube reservoir to be about 3 to 5 inches per second, which maintains adequate mixing without cell damage.

After a determination has been made whether a smear-slide should be produced, usually in about 30 to 60 seconds, the sample portion is discharged from the helical transport, store and mixing reservoir section 73a by coupling the low (5 psi) positive pressure source 85 to open valve 91 through valve 72. The initial 50 microliters of blood, gas region and a lead portion of the trailing segment are discharged through valve 101 pinch valve, pumps 114, 115 and dispensing nozzle to waste. Shortly after detector 79a senses the edge between the trailing end of the lead blood sector and the air sector, the pressure from source 85 is stopped and the pinch valves 114, 115 are actuated to meter a blood drop sample (e.g. about 4 microliters) onto slide S, which is introduced under dispenser 42 by apparatus 40. One preferred construction for such metering is described in concurrently filed U.S. application Ser. No. 08/555,687, entitled "Pinch Pump for Dispensing Fluid from a Flexible Fluid Conduit", which is incorporated herein by this reference. It is to be noted that the storage period has allowed the slide to be appropriately marked and for apparatus 40 to receive other instructions for tailoring the smear procedure to the particular blood sample dispensed. If only one slide is to be made from the specimen from line 73a, the positive pressure is continued to purge the remaining sample into waste 102. After the sample has been moved past valve 76a, it is closed and the appropriate valves (e.g. 88, 93, 77a, 75a, 71, 112, 111) are opened to couple cleaning fluid from fluid source bank 78 through the entire paths just utilized and out into waste 120. Thereafter, the 30 psi air source from bank 78 is coupled to flow through that path and purge and dry the path. One preferred cleaning fluid is a balanced isotonic saline solution such as is commercially available from Coulter Corporation of Miami, Fla. under the tradename ISOTON®. This solution serves to clean the paths of residual blood from the previous sample and is dried or blown out by the 30 psi air purge of the tubing. The residue in the tubing (after blow out and drying) is picked up by the leading segment of the next sample to use that pathway (which leading segment, it will be recalled, is subsequently discarded to waste, also). The exterior of both needle 16 and dispensing probe 42 are also both cleaned and dried after each specimen operation.

After the segment from outlet valve 72 through the dispensing nozzle has been purged with cleaning liquid, the sample reservoir 73b is discharged and metered onto the next successive slide while the reservoir 73a is cleaned and reloaded with the next successive sample.

It will be appreciated that this parallel sequence of loading and cleaning the reservoirs 73a and 73b can continue repeatedly to transport blood samples in a manner maintaining homogeneity, without cell damage.

The invention has been described in detail with particular reference to preferred embodiments thereof, but it will be understood that variations and modifications can be effected within the spirit and scope of invention.

We claim:

1. In an automated blood analysis system comprising a blood analyzer (20) for analyzing a blood specimen to determine constituents thereof, said blood analyzer comprising (i) means (21) for receiving a plurality of blood sample containers, each container containing a blood specimen to be analyzed; (ii) means (32) for aspirating a first portion of said blood specimen from one of said blood sample containers; and (iii) means (22) for analyzing said first blood specimen portion to determine the constituents thereof; the improvement comprising:

(a) a slide maker (40) for automatically producing blood smears on individual microscope slides, said slide maker including slide production control means (10) for causing said aspirating means (32) to aspirate a second portion of said blood specimen from said one of said blood sample containers; a blood drop dispenser (41) for selectively dispensing individual drops of blood on a microscope slide; and slide manipulating and smearing means (42) for smearing a blood drop dispensed on a microscope slide to produce a blood smear on said microscope slide; and (b) specimen transport means (60) interconnecting said blood analyzer and said slide maker, said specimen transport means comprising means for transporting said second blood specimen portion from said aspirating means (32) to said drop dispenser (41), said transport means comprising conduit means (63) forming a fluid coupling between said aspirating means and said drop dispenser, said conduit means defining a generally helical path for blood contained therein, and means (68) for urging blood to flow within said conduit means between said aspirating means and said drop dispenser.

2. The invention defined in claim 1 wherein said second specimen portion is aspirated from substantially the same location within said sample container as was said first specimen portion.

3. The invention defined in claim 1 wherein the aspiration of said second specimen portion is temporally proximate the aspiration of said first specimen portion.

4. The invention defined in claim 3 wherein said second specimen portion is physically and temporally proximate said first specimen portion.

5. The invention defined in claim 1 wherein said blood analyzer comprises control means (10) for controlling said transport means to hold said second specimen portion while said analyzing means analyzes said first specimen portion.

6. The invention defined in claim 5 wherein said control means operates said urging means (68) to cycle said second specimen portion forward and backward along said helical path while said analyzing means (22) analyzes said first specimen portion.

7. The invention defined in claim 1 wherein said receiving means (21) is adapted to receive said plurality of sample containers concurrently, and said analyzing means (22) and said slide maker (40) operate sequentially on a received first container prior to operating on a second received container.

8. The invention defined in claim 1 wherein said transport means (60) aspirates said second specimen portion from one of said sample containers using the same aspirating means that aspirates said first specimen portion.

9. The invention defined in claim 1 further comprising cleaning means for directing cleaning fluids through said conduit means between successive blood specimen passages.

10. The invention defined in claim 10 wherein said conduit means comprises a plurality of separate helical conduits extending in parallel between said aspirating means and said slide maker, and wherein control means operates said blood urging and cleaning means to operate alternately through those separate conduits.

11. The invention defined in claim 1 further including slide identifying means for forming and affixing specimen identifications on said microscope slides.

12. The invention defined in claim 1 wherein said first and second blood specimen portions are aspirated via a common aspirator needle having a pair of parallel fluid channels.

13. In an automated blood analysis system comprising a blood analyzer (20) for analyzing a blood specimen to determine constituents thereof, said analyzer comprising (i) means (21) for receiving a plurality of blood sample containers, each container containing a blood specimen to be analyzed; (ii) means (32) for aspirating a first portion of said blood specimen from one of said blood sample containers; and (iii) means (22) for analyzing said first blood specimen portion to determine the constituents thereof; the improvement comprising:

(a) a slide maker (40) for automatically producing blood smears on individual microscope slides, said slide maker including slide production control means (10) for causing said aspirating means (32) to aspirate a second portion of said blood specimen from said one of said blood sample containers; a blood drop dispenser (41) for selectively dispensing individual drops of blood on a microscope slide; and slide manipulating and smearing means (42) for smearing a blood drop dispensed on a microscope slide to produce a blood smear on said microscope slide; and (b) specimen transport means (60) interconnecting said blood analyzer and said slide maker, said specimen transport means comprising means for transporting said second blood specimen portion from said aspirating means (32) to said drop dispenser (41), said transport means comprising conduit means (63) forming a fluid coupling between said aspirating means and said drop dispenser, said conduit means defining a curvilinear fluid flow path that imparts a substantial angular velocity component to blood cells traveling therealong, and fluid drive means for selectively causing said second blood specimen portion to continuously move along said flow path while said analyzing means operates to analyze said first blood specimen portion.

14. The invention defined in claim 13 wherein said second specimen portion is aspirated from substantially the same location within said sample container as was said first specimen portion.

15. The invention defined by claim 14 wherein said fluid flow path is shaped to cause the tumbling of blood cells comprising said second blood specimen portion as said blood cells move in opposite directions in said flow path.

16. The invention defined by claim 15 wherein said fluid flow path is helically shaped.

17. The invention defined in claim 13 wherein said transport means (60) aspirates said second specimen portion from one of said sample containers using the same aspirating means that aspirates said first specimen portion.

* * * * *